United States Patent [19]

Patsch et al.

[11] Patent Number: 5,260,431
[45] Date of Patent: Nov. 9, 1993

[54] NITROANILINESULFONIC ACIDS AND THE PREPARATION OF PHENYLENEDIAMINESULFONIC ACIDS

[75] Inventors: Manfred Patsch, Wachenheim; Klaus Pandl, Ludwigshafen, both of Fed. Rep. of Germany

[73] Assignee: BASF Aktiengesellschaft, Ludwigshafen, Fed. Rep. of Germany

[21] Appl. No.: 928,088

[22] Filed: Aug. 13, 1992

Related U.S. Application Data

[63] Continuation of Ser. No. 568,199, Aug. 16, 1990, abandoned.

[30] Foreign Application Priority Data

Aug. 16, 1989 [DE] Fed. Rep. of Germany ....... 3927068

[51] Int. Cl.$^5$ ............................................. C07C 309/29
[52] U.S. Cl. ...................................................... 562/73
[58] Field of Search ............................................ 562/73

[56] References Cited

FOREIGN PATENT DOCUMENTS

| | | |
|---|---|---|
| 146889 | 7/1985 | European Pat. Off. . |
| 285972 | 10/1988 | European Pat. Off. . |
| 0294547 | 12/1988 | European Pat. Off. . |
| 0315045 | 5/1989 | European Pat. Off. . |
| 0315046 | 5/1989 | European Pat. Off. . |
| 294547 | 2/1915 | Fed. Rep. of Germany . |

OTHER PUBLICATIONS

Analytische Methoden, pp. 360–365, vol. 11/1, H. Roth, "Analytik von Funktionellen Atomgruppen und Verbindungsklassen".

*Primary Examiner*—Nicky Chan
*Attorney, Agent, or Firm*—Oblon, Spivak, McClelland, Maier & Neustadt

[57] ABSTRACT

Nitroanilinesulfonic acids of the formula

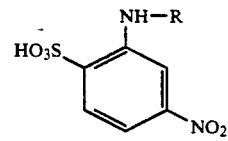

where R is $C_1$–$C_4$-alkyl are prepared by sulfonation of 3-nitro-N-alkylanilines using oleum, and are reduced to 3-(N-alkylamino)aniline-4-sulfonic acids.

1 Claim, No Drawings

NITROANILINESULFONIC ACIDS AND THE PREPARATION OF PHENYLENEDIAMINESULFONIC ACIDS

This application is a continuation of application Ser. No. 07/568,199, filed on Aug. 16, 1990, now abandoned.

The present invention relates to novel nitroanilinesulfonic acids of the formula I

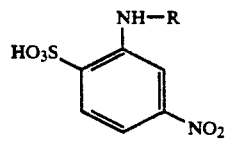

where R is $C_1-C_4$-alkyl.

The preparation of 4-nitro-2-aminobenzenesulfonic acid by sulfonation of 3-nitroaniline with oleum is described in DE-A-294,547.

It is an object of the present invention to provide novel N-alkyl-substituted nitroanilinesulfonic acids.

We have found that this object is achieved by the nitroanilinesulfonic acids of the formula I defined above.

Examples of R in formula I are methyl, ethyl, propyl, isopropyl, butyl, isobutyl or sec-butyl.

Preferred nitroanilinesulfonic acids of the formula I are those in which R is methyl or ethyl.

The nitroanilinesulfonic acids of the formula I according to the invention are valuable intermediates for the preparation of phenylenediaminesulfonic acids of the formula II

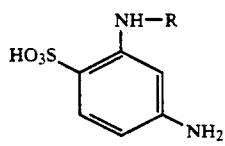

where R has the abovementioned meaning. The latter are in turn suitable for the preparation of valuable copper formazan reactive dyes as are described, for example, in EP-A-315,045 or EP-A-315,046.

Accordingly, the present invention also relates to a process for the preparation of phenylenediaminesulfonic acids of the formula II

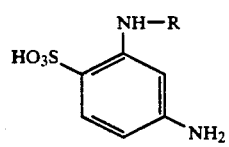

where R is $C_1-C_4$-alkyl, which comprises treating nitroanilines of the formula III

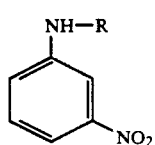

where R has the abovementioned meaning, with oleum and then reducing the resulting nitroanilinesulfonic acids of the formula I

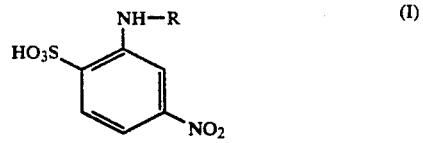

where R has the abovementioned meaning.

The nitroanilines III are generally sulfonated with from 20 to 25% by weight oleum at from 120° to 150° C. 0.5 to 2.0 parts by weight of oleum are normally used per one part by weight of nitroaniline III.

This expediently entails the nitroaniline III first being added to concentrated sulfuric acid and subsequently about 65% by weight oleum being added until the abovementioned concentration is reached. The reaction mixture is heated to the temperature according to the invention and maintained at this f or from 3 to 8 hours and then cooled and poured onto ice. The nitroanilinesulfonic acid I according to the invention precipitates and is removed.

The nitroanilinesulfonic acids I are subsequently reduced by conventional methods as are described, for example, in Houben-Weyl, "Methoden der Organischen Chemie", Volume 11/1, pp. 360 et seq.

Catalytic reduction with hydrogen is preferred, using palladium or, in particular, Raney nickel as catalyst. Palladium is generally used for this in the form of a supported catalyst, in particular on carbon.

The catalytic hydrogenation is generally carried out in an aqueous medium at from 20° to 60° C. under a pressure of from 1.0 to 6.0 bar of hydrogen. The pH is normally from 5 to 11. After uptake of hydrogen has ceased, usually the catalyst is filtered off and the filtrate is acidified. The target product is precipitated and is then removed.

Another preferred method of reduction is with iron by the Béchamp method which is generally carried out at from 50° to 100° C. in an acid medium, preferably in acetic acid. A procedure using from 5 to 20% by weight aqueous acetic acid is particularly preferred.

From 2 to 20 gram atoms of iron are normally used per mole of nitroanilinesulfonic acid.

After the reduction is complete, which normally takes from 1 to 5 hours, the reaction mixture is adjusted to a pH of about 8 to 10 and subsequently filtered. The filtrate is acidified, when the phenylenediaminesulfonic acid is precipitated and is then removed.

The Examples which follow illustrate the invention.

EXAMPLE 1

132 g of 3-nitro-N-methylaniline were added at room temperature to 240 g of concentrated sulfuric acid, during which the temperature rose to 85° C. 138 g of oleum (65% by weight) were added and the mixture was heated to 130° to 140° C. and maintained at this for 5 hours. The solution was cooled and then poured onto 1000 g of ice, and the precipitated 5-nitro-N-methylaniline-2-sulfonic acid was filtered off.

$^{13}$C—NMR data: $\delta(d^6$—DMSO):149.1 (s), 146.1 (s), 136.4 (s), 128.1 (d), 109.3 (d), 104.1 (d), 30.0 (q).

EXAMPLE 2

100 g of 5-nitro-N-methylaniline-2-sulfonic acid were added to a boiling mixture of 1000 g of water, 312 g of iron and 105 g of acetic acid and refluxed for 3 hours. After cooling, the pH was adjusted to 8 with sodium hydroxide solution, and the resulting precipitate was filtered off. The filtrate was acidified to pH 1.0 with hydrochloric acid, and the precipitated 3-(N-methylamino)aniline-4-sulfonic acid was filtered off with suction.

$^{13}$C—NMR data: δ(d$^6$—DMSO): 153.8 (s), 150.5 (s), 131.8 (d), 120.2 (s), 106.2 (d), 100.8 (d), 32.5 (q).

EXAMPLE 3

144 g of 3-nitro-N-ethylaniline were reacted in a similar manner to Example 1. 170 g of 5-nitro-N-ethyl-aniline-2-sulfonic acid were obtained.

$^{13}$C—NMR data: δ(d$^6$—DMSO) :148.9 (s), 145.3 (s), 136.5 (s), 128.2 (d), 108.9 (d), 104.1 (d), 37.5 (t), 14.0 (q).

EXAMPLE 4

100 g of 5-nitro-N-ethylaniline-2-sulfonic acid were reacted in a similar manner to Example 2. 85 g of 3-(N-ethylamino)aniline-4-sulfonic acid were obtained.

$^{13}$C—NMR data: δ(d$^6$—DMSO): 14 2. 7 (s) , 13 7. 7 (s) , 12 8. 6 (s and d) , 10 9. 1 (d), 104.8 (d), 34.4 (t), 13.5 (q).

EXAMPLE 5

23.2 g of 5-nitro-N-methylaniline-2-sulfonic acid were added to 300 g of water. The pH was then adjusted to from 5. 0 to 5.5 with sodium hydroxide solution, 2 g of Raney nickel were added and hydrogenation was carried out under atmospheric pressure at 30° C. After hydrogen uptake had ceased, the catalyst was filtered off, the pH of the filtrate was adjusted to 0.5 to 1.0 with hydrochloric acid, and the precipitated 3-(N-methylamino)aniline-4-sulfonic acid was isolated by filtration.

EXAMPLE 6

The procedure of Example 5 was carried out but using 24.6 g of 5-nitro-N-ethylaniline-2-sulfonic acid. 21.0 g of 3-(N-ethylamino)aniline-4-sulfonic acid were obtained.

We Claim:

1. A nitroanilinesulfonic acid of the formula I

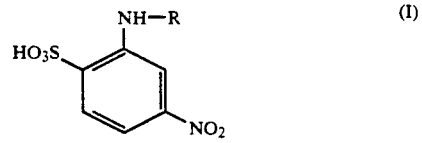

where R is C$_1$–C$_4$-alkyl.

* * * * *